United States Patent

Hofer et al.

[11] 4,146,632
[45] Mar. 27, 1979

[54] COMBATING PESTS WITH N,N-DIMETHYL-O-[3-TERT.-BUTYL-PYRAZOL-5-YL]-CARBAMIC ACID ESTERS

[75] Inventors: Wolfgang Hofer; Fritz Maurer; Hans-Jochem Riebel, all of Wuppertal; Rolf Schröder, Velbert; Ingeborg Hammann, Cologne; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 833,938

[22] Filed: Sep. 16, 1977

[30] Foreign Application Priority Data

Oct. 2, 1976 [DE] Fed. Rep. of Germany ....... 2644589

[51] Int. Cl.$^2$ .................... C07D 231/20; A01N 9/22
[52] U.S. Cl. ................. 424/273 P; 548/375; 548/376; 548/365; 548/367
[58] Field of Search ............ 548/375, 376, 377; 424/273 P

[56] References Cited

U.S. PATENT DOCUMENTS 2,681,915  6/1954  Gysia et al. ............ 548/375
3,415,933  12/1968  Gubler ................. 424/273 P

FOREIGN PATENT DOCUMENTS 279553  3/1952  Switzerland ............ 548/377
282655  8/1952  Switzerland ............ 548/377
414249  12/1966  Switzerland ............ 548/375
1092696  11/1967  United Kingdom ........ 548/377

Primary Examiner—Natalie Trousof
Assistant Examiner—Natalia Harkaway
Attorney, Agent, or Firm—Sprung, Felfe, Horn, Lynch & Kramer

[57] ABSTRACT

N,N-dimethyl-O-[3-tert.-butylpyrazol-5-yl]-carbamic acid esters of the formula

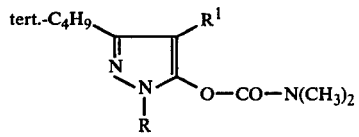

in which
R represents hydrogen, alkyl or cyanoalkyl and
$R^1$ represents hydrogen, halogen or alkyl which possess arthropodicidal and nematicidal properties.

7 Claims, No Drawings

COMBATING PESTS WITH N,N-DIMETHYL-O-[3-TERT.-BUTYLPYRAZOL-5-YL]-CARBAMIC ACID ESTERS

The present invention relates to and has for its objects the provision of particular new N,N-dimethyl-O-[3-tert.-butylpyrazol-5-yl]-carbamic acid esters which possess arthropodicidal and nematicidal properties, active compositions in the form of mixtures of such compounds with solid and liquid dispersible carrier vehicles, and methods for producing such compounds and for using such compounds in a new way especially for combating pests, e.g. arthropods and nematodes, with other and further objects becoming apparent from a study of the within specification and accompanying examples.

It is known from Swiss Patent Specifications Nos. 282,655, 281,967 and 279,553 that certain N,N-dimethyl-O-pyrazolylcarbamic acid esters, for example N,N-dimethyl-O-[1-phenyl-3-methyl-(Compound B) and 1-isopropyl-3-methyl-pyrazol-5-yl] carbamic acid ester (Compound A) possess insecticidal properties.

The present invention now provides, as new compounds, the tert.-butyl-substituted pyrazolylcarbamic acid esters of the general formula

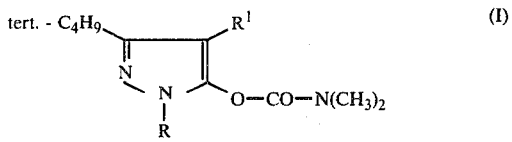

in which

R represents hydrogen, alkyl or cyanoalkyl and
R$^1$ represents hydrogen, halogen or alkyl.

Preferably, R represents hydrogen, or straight-chain or branched alkyl or cyanoalkyl, in either case with 1 to 4 (especially 1 or 2) carbon atoms in the alkyl radical and R$^1$ represents chlorine, bromine, hydrogen or straight-chain or branched alkyl with 1 to 4 carbon atoms (especially methyl).

Surprisingly, the tert.-butyl-substituted pyrazolylcarbamic acid esters of the formula (I) exhibits a better insecticidal and nematicidal action than the known pyrazolylcarbamic acid esters of analogous structure and of the same type of action. The compounds according to the invention thus represent a genuine enrichment of the art.

The invention also provides a process for the preparation of a tert.-butyl-substituted pyrazolylcarbamic acid ester of the formula (I) in which a 3-tert.-butyl-5-hydroxypyrazole of the general formula

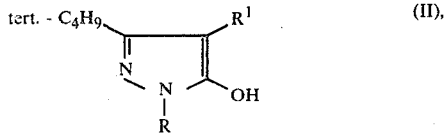

in which R and R$^1$ have the above-mentioned meanings, is reacted, either as such in the presence of an acid acceptor or in the form of an alkali metal salt, alkaline earth metal salt or ammonium salt, with N,N-dimethyl-carbamic acid chloride, of the formula

in the presence of a solvent or diluent.

If, for example, 1-methyl-3-tert.-butyl-5-hydroxypyrazole and N,N-dimethyl-carbamic acid chloride are used as starting materials, the course of the reaction can be represented by the following equation:

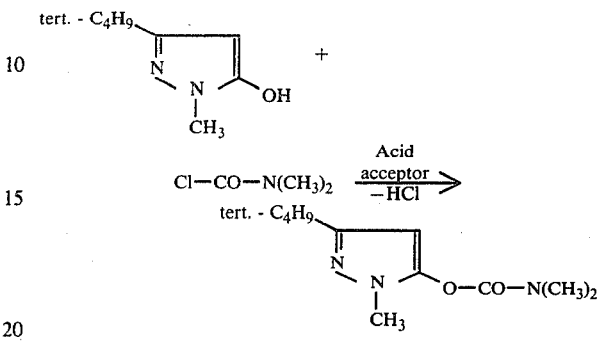

N,N-Dimethyl-carbamic acid chloride (III), to be used as a starting material, is known from the literature and can readily be prepared in accordance with customary processes, as can the tert.-butyl-substituted 5-hydroxy-pyrazoles (II), which are obtained by reacting pivaloylacetic acid alkyl esters with hydrazine derivatives, if appropriate in the presence of an alcoholate. The following may be mentioned as individual examples: 3-tert.-butyl-, 1-methyl-3-tert.-butyl-, 1-ethyl-3-tert.-butyl-, 1-(2-cyanoethyl)-3-tert.-butyl-, 1-methyl-3-tert.-butyl-4-chloro-, 1-ethyl-3-tert.-butyl-4-chloro-, 1-(2-cyanoethyl)-3-tert.-butyl-4-chloro-, 1-methyl-3-tert.-butyl-4-bromo-, 1-ethyl-3-tert.-butyl-4-bromo-, 1-(2-cyanoethyl)-3-tert.-butyl-4-bromo-, 1,4-dimethyl-3-tert.-butyl-, 1-ethyl-3-tert.-butyl-4-methyl-, 1-(2-cyanoethyl)-3-tert.-butyl-4-methyl-, 3-tert.-butyl-4-chloro-, 3-tert.-butyl-4-bromo- and 3-tert.-butyl-4-methyl-5-hydroxy-pyrazole.

The process for the preparation of the compounds according to the invention is carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from 0° to 100° C., preferably at from 10° to 70° C.

In general, the reaction is allowed to take place under normal pressure.

To carry out the process, the starting components are in most cases employed in equimolar amounts. An excess of one or other reactant produces no significant advantages. In most cases, the reactants are brought together in one of the above-mentioned solvents in the presence of an acid acceptor and stirred in most cases at an elevated temperature for one or several hours in order to complete the reaction. The reaction solution is then cooled and filtered and the filtrate is concentrated. The residue is taken up in an organic solvent, for example toluene, the latter is washed with water and dried, and the solvent is distilled off.

The new compounds are obtained in the form of oils, which in most cases cannot be distilled without decomposition, but are freed from the last volatile constituents by socalled "slight distillation", that is to say by prolonged heating under reduced pressure to moderately elevated temperatures, and are purified in this way. They are characterized by the refractive index.

As already mentioned, the tert.-butyl-substituted pyrazolylcarbamic acid esters according to the invention are distinguished by an excellent insecticidal and nematicidal activity.

The active compounds are well tolerated by plants, have a favorable level of toxicity to warm-blooded animals, and can be used for combating arthropod pests, especially insects which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Seutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua recticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus ololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of Siphonaptera, for example *Xenopsylla cheopis* and Ceratophyllus spp.

The plant-parasitic nematodes include Pratylenchus spp., *Radopholus similis, Ditylenchus dipsaci, Tylenchulus semipenetrans,* Heterodera spp., Meloidogyne spp., Aphelenchloides spp., Longidorus spp., Xiphinema spp., and Trichodorus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutions, emulsions, suspension, powders, pastes, and granules which are thus ready for use.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. arthropods and nematodes, which comprises applying to at least one of correspondingly (a) such acarids, (b) such nematodes, and (c) the corresponding habitat thereof, i.e. the locus to be protected, e.g. to a growing crop, to an area where a crop is to be grown or to a domestic animal, a corresondingly combative or toxic amount, arthropodicidally an arthroodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The process of the present invention is illustrated by the following preparative examples:

EXAMPLE 1

(a)

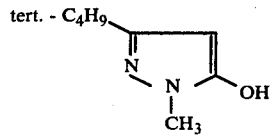

9.2 g (0.2 mol) of methylhydrazine were added dropwise to a mixture of 34.4 g (0.2 mol) of pivaloylacetic acid ethyl ester, 10.8 g (0.2 mol) of sodium methylate and 100 ml of methanol at 20° C. After the exothermic reaction had subsided, the mixture was heated for two hours under reflux. The reaction mixture was then concentrated, the residue was taken up in 200 ml of water and this solution was acidified to pH 6 with concentrated hydrochloric acid. The resulting precipitate was filtered off, dried and recrystallized from isopropanol. 27 g (87% of theory) of 1-methyl-3-tert.-butyl-5-hydroxy-pyrazole were obtained in the form of colorless crystals with a melting point of 150° C.

The following compounds of the formula

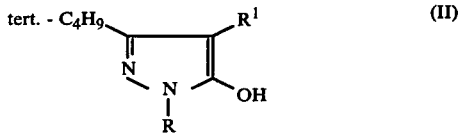

could be prepared analogously:

TABLE 1

| Intermediate | R | R$^1$ | Yield (% of theory) | Melting Point ° C. |
| --- | --- | --- | --- | --- |
| (ii) | CH$_3$ | CH$_3$ | | |
| (iii) | CH$_3$ | Br | | |
| (iv) | CH$_3$ | Cl | 50 | 155 |
| (v) | H | H | 71 | 202 |

(b)

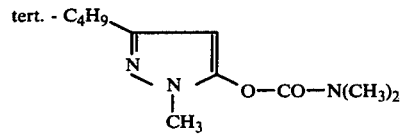

10.7 g (0.1 mol) of N,N-dimethyl-carbamic acid chloride were added dropwise to a mixture of 15.4 g (0.1 mol) of 1-methyl-3-tert.-butyl-5-hydroxy-pyrazole, 14.5 g (0.105 mol) of potassium carbonate and 200 ml of acetonitrile at 20° C. and the batch was stirred for a further 3 hours at 60° C. The reaction mixture was then cooled and filtered and the filtrate was concentrated. The residue was taken up in 200 ml of toluene, the organic phase was washed once with 100 ml, of water and dried over sodium sulphate, and the solvent was distilled off. 15 g (61% of theory) of N,N-dimethyl-O-[1-methyl-3-tert.-butylpyrazol-5-yl]-carbamic acid ester were obtained in the form of a brown oil having a refractive index $n_D^{22}$ of 1.4860.

The following compounds of the formula

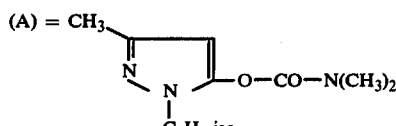

could be synthesized analogously:

Table 2

| Compound No. | R | R$^1$ | Yield (% of theory) | Physical data (refractive index; melting point ° C.) |
| --- | --- | --- | --- | --- |
| 2 | CH$_3$ | CH$_3$ | | |
| 3 | CH$_3$ | Br | | |
| 4 | H | H | 99 | 132 |
| 5 | —CH$_2$—CH$_2$—CN | H | 95 | $n_D^{23}$:1,4930 |
| 6 | CH$_3$ | Cl | 58 | $n_D^{24}$:1,5030 |

The insecticidal and nematicidal activity of the compounds of this invention is illustrated by the following examples wherein the compounds according to the present invention are each identified by the number (given in brackets) from the preparative example hereinabove.

The known comparison compounds are identified as follows:

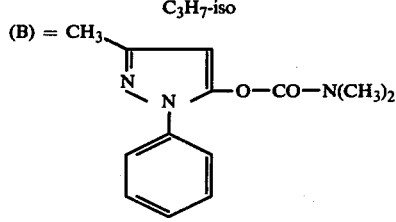

EXAMPLE 2

Myzus test (contact action)

Solvent: 3 parts by weight of dimethylformamide

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

Table 3

(Insects which damage plants)
*Myzus* test

| Active compounds | Active compound concentration in % | Degree of destruction in % after 1 day |
|---|---|---|
| (A) | 0.1 | 100 |
|  | 0.01 | 0 |
| (B) | 0.1 | 98 |
|  | 0.01 | 0 |
| (1) | 0.1 | 100 |
|  | 0.01 | 100 |
| (4) | 0.1 | 100 |
|  | 0.01 | 99 |
| (5) | 0.1 | 100 |
|  | 0.01 | 100 |

EXAMPLE 3

Root-systemic action
Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (= mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

The active compounds, the amounts used and the results can be seen from the following table:

Table 4

(root-systemic action)
*Phaedon cochleariae* larvae

| Active compounds | Degree of destruction in % at an active compound concentration of 20 ppm |
|---|---|
| (B) | 0 |
| (4) | 100 |
| (1) | 100 |

EXAMPLE 4

Test namatode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (= mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 5

(Nematicides)
*Meloidogyne incognita*

| Active compounds | Degree of destruction in % at an active compound concentration of 20 ppm |
|---|---|
| (B) | 0 |
| (4) | 100 |
| (1) | 100 |

EXAMPLE 5

$LT_{100}$ test for Diptera
Test insects: *Musca domestica* and *Aedes aegypti*
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was continuously observed. The time which was necessary for 100% destruction was determined.

The active compounds, the concentrations of the active compounds and the times at which there was 100% destruction can be seen from the following table:

Table 6

| | (LT₁₀₀ test for Diptera) | | |
|---|---|---|---|
| | *Musca domestica* and *Aedes aegypti* | | |
| Active compounds | Test insects | Active compound concentration of the solution in % | $LT_{100}$ |
| (B) | *Musca domestica* | 0.2 | 8 hrs 0% |
| | *Aedes aegypti* | 0.02 | 3 hrs 0% |
| (1) | *Musca domestica* | 0.02 | 90' |
| | *Aedes aegypti* | 0.002 | 60' |

EXAMPLE 6

Test with parasitic fly larvae
Solvent: 35 parts by weight of ethylene polyglycol monomethyl ether
Emulsifier: 35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (*Lucilia cuprina*) were introduced into a test tube which contained approximately 2 ml of horse muscle. 0.5 ml of the preparation of active compound was applied to this horse meat. After 24 hours, the degree of destruction in % was determined. 100% meant that all of the larvae had been killed and 0% meant that none of the larvae had been killed.

The active compounds, the concentrations of the active compounds and the results can be seen from the table which follows:

Table 7

| | (Test with parasitic fly larvae/ *Lucilia cuprina* res.) | |
|---|---|---|
| Active compound | Active compound concentration in ppm | Destructive action in % |
| (4) | 1,000 | 100 |
| | 100 | 100 |
| | 10 | 0 |

It will be appreciated that the instant specification and examples are set forth by way of illustration and not limitation, and that various modifications and changes may be made without departing from the spirit and scope of the present invention.

What is claimed is:

1. An N,N-dimethyl-O-[3-tert.-butylpyrazol-5-yl]-carbamic acid ester of the formula

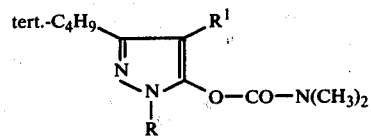

in which
R represents hydrogen, or alkyl or cyanoalkyl with 1 to 4 carbon atoms in either alkyl radical, and
$R^1$ represents halogen.

2. An ester according to claim 1, in which R represents hydrogen, methyl or cyanoethyl.

3. An ester according to claim 1, wherein such ester is N,N-dimethyl-O-[4-chloro-1-methyl-3-tert.-butyl-pyrazol-5-yl]-carbamic acid ester of the formula

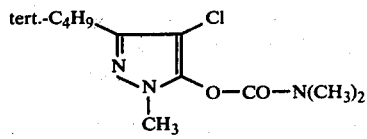

4. An arthropodicidal or nematicidal composition containing as active ingredient an arthropodicidally or nematicidally effective amount of a compound according to claim 1 in admixture with a diluent.

5. A method of combating anthropods or nematodes which comprises applying to the arthropods or nematodes, or to a habitat thereof, an arthropodicidally or nematicidally effective amount of a compound according to claim 1.

6. The method according to claim 5 in which said compound is applied to a domesticated animal.

7. The method according to claim 5, in which said compound is
N,N-dimethyl-O-[4-chloro-1-methyl-3-tert.-butyl-pyrazol-5-yl]-carbamic acid ester.

* * * * *